United States Patent
Radwanski

(10) Patent No.: US 10,213,544 B2
(45) Date of Patent: Feb. 26, 2019

(54) METHODS FOR TREATING A SUSPENSION OF MONONUCLEAR CELLS TO FACILITATE EXTRACORPOREAL PHOTOPHERESIS

(71) Applicant: FENWAL, INC., Lake Zurich, IL (US)

(72) Inventor: Katherine Radwanski, Des Plaines, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 13/916,854

(22) Filed: Jun. 13, 2013

(65) Prior Publication Data

US 2014/0370491 A1    Dec. 18, 2014

(51) Int. Cl.
*A61M 1/36* (2006.01)
*A61M 1/34* (2006.01)

(52) U.S. Cl.
CPC ........ *A61M 1/3681* (2013.01); *A61M 1/3686* (2014.02); *A61M 1/3692* (2014.02); *A61M 1/3696* (2014.02); *A61M 1/3496* (2013.01); *A61M 1/3683* (2014.02); *A61M 1/3693* (2013.01); *A61M 2202/0439* (2013.01); *A61M 2205/053* (2013.01)

(58) Field of Classification Search
None
See application file for complete search history.

(56) References Cited

U.S. PATENT DOCUMENTS

| | | | |
|---|---|---|---|
| 4,683,889 A * | 8/1987 | Edelson | ............ 607/92 |
| 6,027,657 A | 2/2000 | Min et al. | |
| 6,219,584 B1 | 4/2001 | Lee | |
| 2004/0209377 A1 | 10/2004 | Crews et al. | |

OTHER PUBLICATIONS

Gatza et al., BLOOD, vol. 112, No. 4, 2008, pp. 1515-1521.*
Ward et al., Journal of Clinical Apheresis, vol. 26, pp. 276-285, 2011.*
Sigma Red Blood Cell Lysing Buffer Hybri-Max, retrieved from the Internet: www.sigmaaldrich.com/catalog/product/sigma/r7757?lang=en&region=US.*
BD Biosciences, BD Pharm Lyse TM, Technical Data Sheet, Lysing Buffer, Instructions for use, Copyright 2008, 2 pages.
European Patent Office, European Search Report dated Feb. 13, 2015, Application No./Patent No. 13188736.6-1651 / 2813253. Applicant/Proprietor: Fenwal, Inc., 6 pages.

* cited by examiner

*Primary Examiner* — Thomas J. Visone
*Assistant Examiner* — Evelyn Y Pyla
(74) *Attorney, Agent, or Firm* — Cook Alex Ltd.

(57) ABSTRACT

A method for performing a photopheresis procedure is provided comprising collecting MNCs in a suspension comprising RBCs and plasma and lysing the red blood cells in the solution, preferably by combining the suspension with a solution to cause lysis. In one example, the solution for causing lysis of the red blood cells comprises ammonium chloride, and the suspension including the ammonium chloride is incubated to cause lysing. After lysing, the suspension may be washed to remove plasma and hemoglobin freed by the lysis of the red blood cells, and an ultraviolet light activated substance is added to the suspension. The suspension is then irradiated with ultraviolet light.

12 Claims, 5 Drawing Sheets

METHODS FOR TREATING A SUSPENSION OF MONONUCLEAR CELLS TO FACILITATE EXTRACORPOREAL PHOTOPHERESIS

FIELD OF THE DISCLOSURE

The present disclosure is directed to a method for performing extracorporeal photopheresis of mononuclear cells (MNCs) and, more particularly, to a method for treating a suspension of mononuclear cells to reduce the amount of light attenuating medium in the suspension.

Light irradiation therapy is used for the treatment of various blood diseases to, e.g., eliminate immunogenicity in cells, inactivate or kill selected cells, inactivate viruses or bacteria, or activate desirable immune responses. For example, it is known to use the photoactivatable drug psoralen to treat pathogenic blood cells, such as lymphocytes, in an extracorporeal photopheresis (ECP) procedure in which blood is withdrawn from the patient, cells are separated (typically by centrifugation), 8-methoxypsoralen (8-MOP) is added to the cells which are then subjected to UV light to activate the 8-MOP molecules. The UV light crosslinks 8-MOP to DNA strands inside the cell and on the cell wall of the pathogenic leukocytes, eventually causing apoptosis. The fluid with the altered leukocytes is reinfused back into the patient to induce an immune system response.

A difficulty in performing phototherapy is the delivery of the proper dose of light energy to the photoactivatable material in the suspension, particularly if the suspension includes material (such as red blood cells) that is not substantially transparent to light so that it attenuates the light energy intended for photoactivation.

A method for delivering a desired dose of light energy to a suspension is disclosed in U.S. Pat. No. 6,219,584. This patent is directed to an "online" photopheresis system that includes both the blood separation device and the photoactivation device in an integrated, closed system. In the system described in U.S. Pat. No. 6,219,584, a complex algorithm is used to determine the emitted dose ("fluid light energy value" or FLEV) needed to achieve the target dose (the "target's effective light energy value" or TELEV) that is to be delivered to the targeted leukocytes (mononuclear cells or MNC). This algorithm requires knowledge of the thickness ratio of the product, as well as the light transmittance value of the product is measured for every product using a hematocrit sensor.

In "offline" methods, (such as those practiced when using the phototherapy systems available from Macopharma SA or Vilber Lourmet), the UV dose is monitored by sensors which are angled to detect UV light emitted from the UV bulbs as well as that reflected from the mirrored surface behind each set of bulbs (and presumably less light is reflected back if the treated cell product is absorbing more light). This method does not fully account for the UV light being absorbed by the red cells and plasma, and operators are required to manually measure the product hematocrit and adjust it (if necessary) to lower than 2% because the UV dose delivered at higher hematocrits is unknown (and likely insufficient).

In accordance with the method described below, a method of performing ECP is provided in which the suspension of MNCs is treated prior to photoactivation to substantially reduce the amount of light attenuating material in the suspension, so that the amount of UV light being absorbed corresponds more closely to the dose being emitted, thus providing for a more precise therapeutic result than simply applying a correction factor to the emitted light dose.

SUMMARY OF THE DISCLOSURE

In accordance with one aspect of the disclosure, a method of extracorporeal photopheresis of mononuclear cells in a suspension that includes red blood cells is provided. The method comprises lysing red blood cells in a suspension; removing from the suspension hemoglobin freed by the lysing of the red blood cells; adding an ultraviolet light activated substance to the suspension; and irradiating the suspension with ultraviolet light. The lysing does not substantially adversely affect the viability of the mononuclear cells in the suspension.

In a further aspect, the step of lysing includes the addition of a lysing agent to the suspension. The lysing preferably comprises the addition of ammonium chloride to the suspension, and, more specifically, the addition of an aqueous suspension of ammonium chloride at a predetermined concentration. The predetermined concentration is preferably from about 100 mM to 200 mM.

In a related aspect, in which the suspension includes plasma, the method further comprises removing plasma from the suspension. Preferably, the plasma and hemoglobin are removed substantially simultaneously, and the removal may be accomplished by washing.

In another aspect, the method comprises incubating the solution and lysing agent before removing hemoglobin. In a preferred embodiment removal of hemoglobin is accomplished by centrifuging the solution.

In a further aspect, the ultraviolet light activated substance comprises psoralen. Preferably, the ultraviolet light activated substance comprises 8-methoxypsoralen.

In another aspect, the suspension is irradiated with UVA ultraviolet light. Preferably, the suspension is irradiated with ultraviolet light for five minutes or less.

According to the present disclosure, a method is also provided for performing extracorporeal photopheresis of mononuclear cells. The method comprises collecting mononuclear cells in a suspension comprising red blood cells and plasma; combining the suspension with a solution to cause lysis of the red blood cells; removing from the suspension plasma and hemoglobin freed by the lysis of the red blood cells; adding an ultraviolet light activated agent to the suspension; and irradiating the suspension with ultraviolet light. Preferably, the removal of plasma and hemoglobin freed by the lysis of the red blood cells is accomplished by washing the suspension by centrifugation. Further, the solution for causing lysis of the red blood cells comprises ammonium chloride, and the suspension including the ammonium chloride is incubated.

In another aspect, a method of extracorporeal photopheresis of mononuclear cells in a suspension of concentrated mononuclear cells that includes red blood cells and plasma is provided that comprises removing sufficient red blood cells from the suspension to substantially decrease absorption of ultraviolet light by non-target substances in the suspension; adding an ultraviolet light activated substance to the suspension; and, irradiating the suspension with ultraviolet light. Preferably, the residual red blood cells are removed by either immunomagnetic cell separation or density gradient separation of the suspension.

Other aspects of the disclosure will become apparent upon references to the accompanying figures and following detailed description.

DESCRIPTION OF THE ILLUSTRATED EMBODIMENTS

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

A method for performing a photopheresis procedure is described below. The method generally comprises collecting MNCs in a suspension that includes a quantity of residual red blood cells and plasma, and lysing (i.e., disintegrating) the red blood cells in the solution, preferably by combining the suspension with a solution that causes lysis. The lysing does not substantially adversely affect the viability of the mononuclear cells in the suspension. In one example, the solution for causing lysis of the red blood cells comprises ammonium chloride, and the suspension including the ammonium chloride is incubated to cause lysing. After lysing, the suspension may be washed to remove plasma and hemoglobin freed by the lysis of the red blood cells. The ultraviolet light activated substance is added to the suspension, and the suspension is then irradiated with ultraviolet light.

Figure 1:
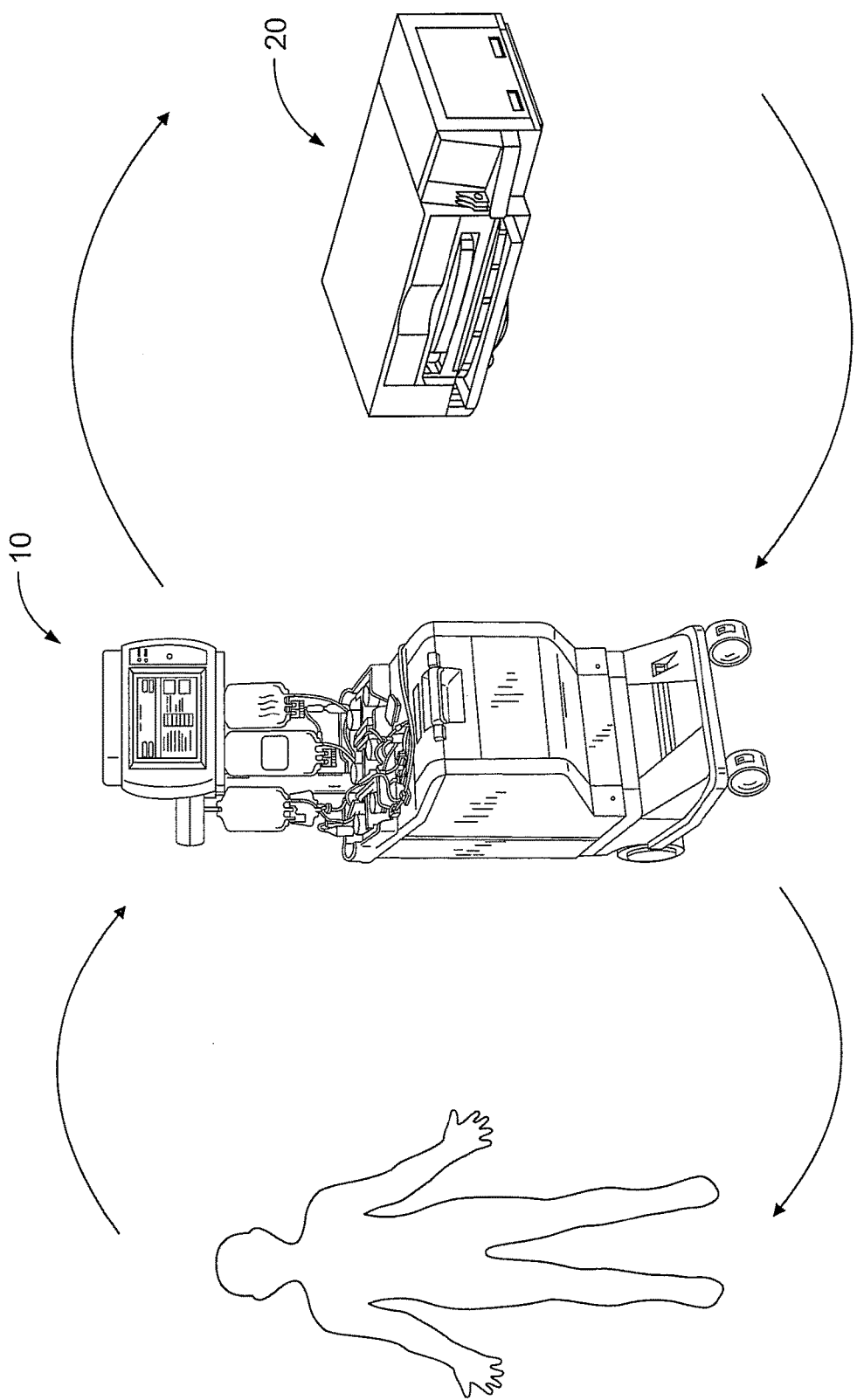
FIG. 1 is a diagram generally showing the mechanical components of an exemplary photopheresis treatment as described herein.

FIG. 1 shows, generally, the mechanical components that make up a system that may be used in the methods described herein. In accordance with the present disclosure, the system includes a separation component 10 and a treatment (i.e., irradiation) component 20. Preferably, irradiation component 20 is independent and housed separately from separation component 10. Although separately housed and independent devices, it is preferable that separation device 10 and irradiation device 20 are located adjacent to each other. While FIG. 1 shows a preferred embodiment of separated separation and irradiation components, it will be appreciated that the methods described herein may also be used with devices having integrated separation and irradiation components.

Figure 4:
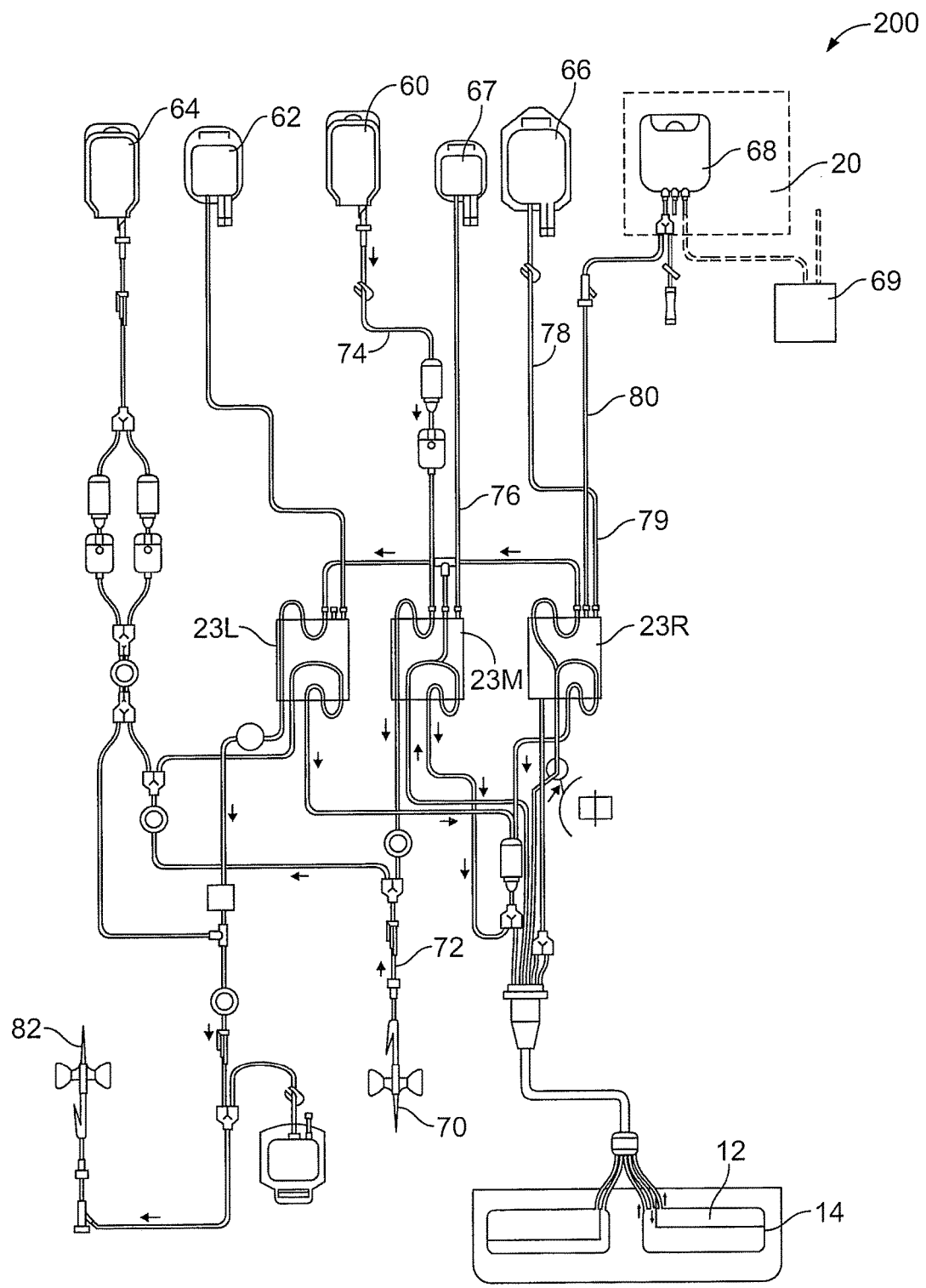
FIG. 4 is a diagram of the fluid circuit useful in the collection, treatment and reinfusion of mononuclear cells as described herein.

In accordance with the systems and methods described herein a patient is connected to a blood processing set, i.e., fluid circuit 200. As generally illustrated in FIGS. 1 and 4, fluid circuit 200 provides a sterile closed pathway between separation component 10 and irradiation component 20. The system described herein also optionally includes a washing component which, preferably, is housed within the separation component. Preferably, the separation component 10 and washing component are one and the same.

With reference to FIG. 1, whole blood is withdrawn from the patient and introduced into the separation component 10 where the whole blood is separated to provide a target cell population. In a preferred embodiment in accordance with the present disclosure, the target cell population is mononuclear cells. (While the collection of mononuclear cells is described as being accomplished by apheresis, manual methods may also be used.) Other components separated from the whole blood in this initial separation, such as red blood cells and platelets, may be returned to the patient or collected in pre-attached containers of the blood processing set.

The separated target cell population, e.g., mononuclear cells with residual red blood cells and plasma, is then prepared for treatment and irradiation in treatment component 20. As discussed above, treatment of mononuclear cells involves the photoactivation of a photoactive agent that has been combined with the mononuclear cells. Once treated, the mononuclear cells may optionally be provided to a washing component, which, as shown in FIG. 1, is housed within separation component 10. The treated mononuclear cells are separated from the supernatant and the concentrated cells may be returned to the patient. The supernatant liquid will typically include excess and unbound photoactivation agent. Optionally, the concentrated cells may further be combined with a suitable wash solution within separation/washing component 10. If washing of the treated mononuclear cells is performed, the suspension of mononuclear cells in a wash solution is then subjected to a centrifugal field (or other environment which can effect separation of the fluid components), whereby the mononuclear cells are concentrated and separated from the supernatant, including any remaining unbound photoactivation agent. Supernatant may then be diverted to an appropriate waste container, while the treated mononuclear cells are returned to the patient, as generally shown in FIG. 1.

Figure 2:
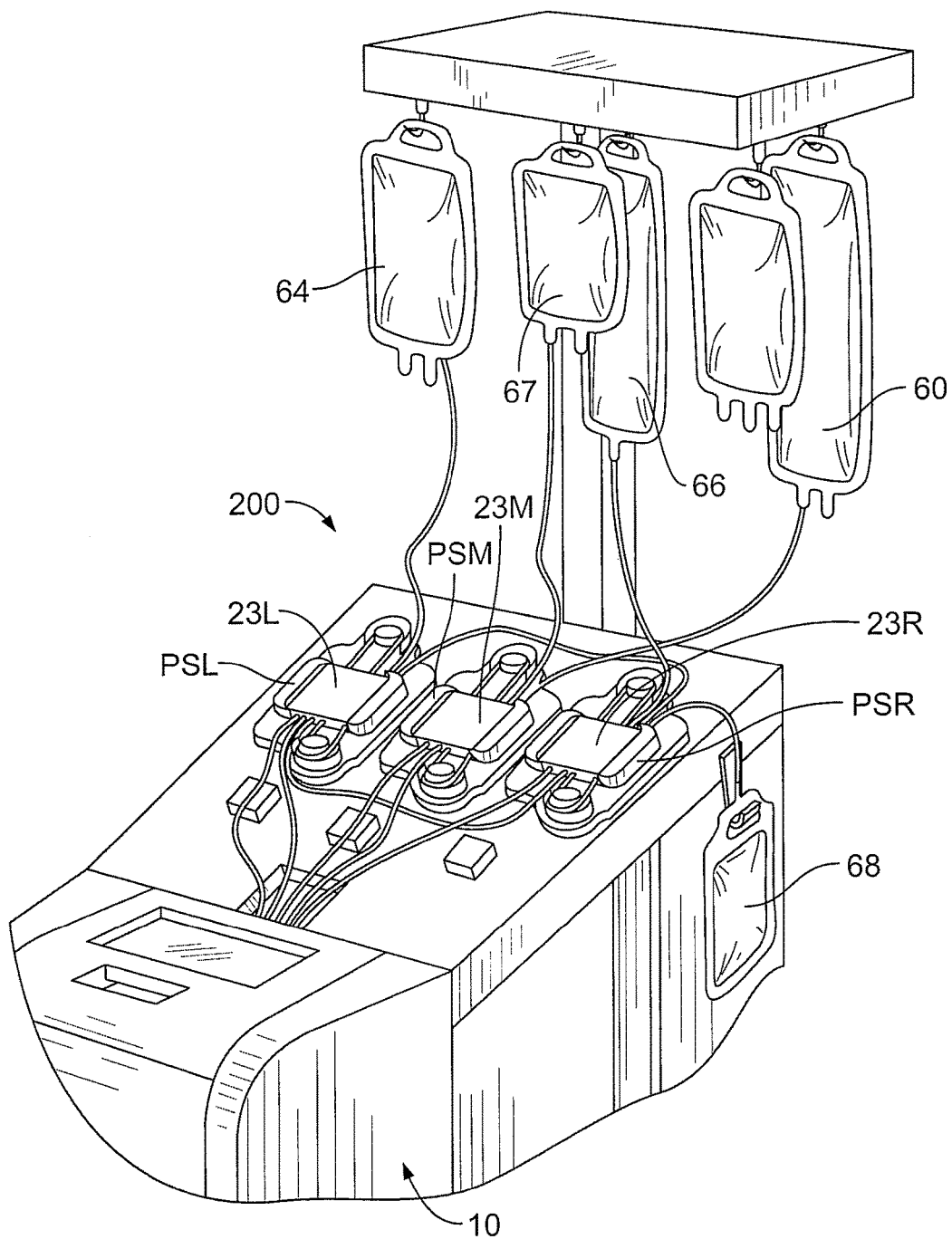
FIG. 2 is a partial perspective view of a multifunctional apheresis separator useful in the methods and systems described herein.
Figure 3:
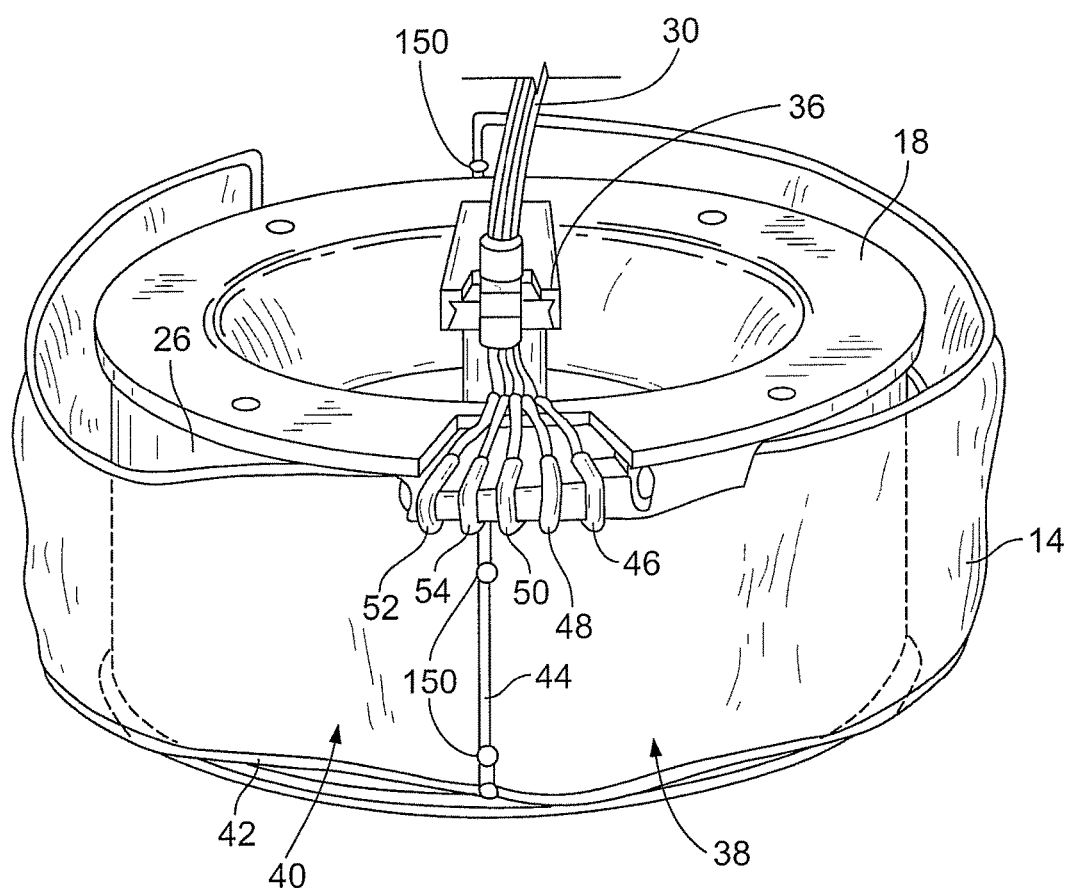
FIG. 3 is a perspective view of a processing container (separation chamber) of the processing set used with the separator of FIG. 2.

Apparatus useful in the collection (and washing) of mononuclear cells, and providing the separation component 10 of FIG. 1, include the AMICUS® separator made and sold by Fenwal, Inc., of Lake Zurich, Ill. Mononuclear cell collections using a device such as the AMICUS® separator are described in greater detail in U.S. Pat. No. 6,027,657, the contents of which is incorporated by reference herein in its entirety. Briefly, FIGS. 2-4 show a representative blood centrifuge 10 with fluid circuit 200 mounted thereon (FIG. 2), the fluid circuit (FIG. 4) having a blood processing container 14 (see FIG. 3) defining a separation chamber suitable for harvesting mononuclear cells from whole blood. As shown in FIG. 2, a disposable processing set or fluid circuit 200 (which includes container 14) is mounted on the front panel of centrifuge 10. The processing set (fluid circuit 200) includes a plurality of processing fluid flow cassettes 23L, 23M and 23R with tubing loops for association with peristaltic pumps on device 10. Fluid circuit 200 also includes a network of tubing and pre-connected containers for establishing flow communication with the patient and for processing and collecting fluids and blood and blood components, as shown in greater detail in FIG. 4.

As seen in FIGS. 2 and 4, disposable processing set 200 may include a container 60 for supplying anticoagulant, a waste container 62 for collecting waste from one or more steps in the process for treating and washing mononuclear cells, a container 64 for holding saline or other wash or re-suspension medium, a container 66 for collecting plasma, a container 68 for collecting the mononuclear cells and, optionally, container 69 for holding the photoactivation agent.

Container 68 may also serve as the illumination container, and is preferably pre-attached to with the disposable set 200. Alternatively, container 68 may be attached to set 200 by known sterile connection techniques, such as sterile docking or the like. With reference to FIG. 4, fluid circuit includes inlet line 72, an anticoagulant (AC) line 74 for delivering AC from container 60, an RBC line 76 for conveying red blood cells from chamber 12 of container 14 to container 67, a platelet-poor plasma (PPP) line 78 for conveying PPP to container 66 and line 80 for conveying mononuclear cells to and from separation chamber 14 and collection/illumination container 68. The blood processing set includes one or more venipuncture needle(s) for accessing the circulatory system of the patient. As shown in FIG. 4, fluid circuit 200 includes inlet needle 70 and return needle 82. In an alternative embodiment, a single needle can serve as both the inlet and outlet needle.

Container 68 is suitable for irradiation by light of a selected wavelength. By "suitable for irradiation" it is meant that the walls of the container are sufficiently transparent to light of the selected wavelength to activate the photoactive agent. In treatments using UVA light, for example, container walls made of ethylene vinyl acetate (EVA) are suitable. Accordingly, container 68 in which the mononuclear cells are collected may serve both as the collection container and the irradiation container. Container 68 may be placed inside irradiation device 20 by the operator or, more preferably, may be placed inside the irradiation chamber of irradiation device 20 at the beginning of the ECP procedure and prior to whole blood withdrawal (as shown by the broken lines representing device 20 in FIG. 4). In any event, container 68 preferably remains integrally connected to the remainder of fluid circuit 200 during the entire procedure, thereby maintaining the closed or functionally closed condition of fluid circuit 200.

Fluid flow through fluid circuit 200 is preferably driven, controlled and adjusted by a microprocessor-based controller in cooperation with the valves, pumps, weight scales and sensors of device 10 and fluid circuit 200, the details of which are described in the previously mentioned U.S. Pat. No. 6,027,657.

The fluid circuit is further adapted for association with the treatment component (i.e., irradiation device) 20. Apparatus for the irradiation of the mononuclear cells are also known and are available from sources such as Cerus Corporation, of Concord, Calif. One example of a suitable irradiation device is described in U.S. Pat. No. 7,433,030, the contents of which is likewise incorporated by reference herein in its entirety. As shown and described in U.S. Pat. No. 7,433,030, irradiation device preferably includes a tray or other holder for receiving one or more containers during treatment. Other irradiation devices may also be suitable for use with the method and system described herein, including devices available from Macopharma and/or Vilber Lourmet.

As noted above, separation chamber 12 is defined by the walls of a flexible processing container 14 carried within an annular gap defined by a rotating spool element 18 and an outer bowl element (not shown). The processing container 14 takes the form of an elongated tube which is wrapped about the spool element 18 before use. The bowl and spool element 18 are pivoted on a yoke between an upright position and a suspended position, also not shown. In operation, the centrifuge 10 rotates the suspended bowl and spool element 18 about an axis 28, creating a centrifugal field within the processing chamber of container 14. Details of the mechanism for causing relative movement of the spool 18 and bowl elements as just described are disclosed in U.S. Pat. No. 5,360,542 entitled "Centrifuge with Separable Bowl and Spool Elements Providing Access to the Separation Chamber," which is also incorporated herein by reference.

In accordance with the present disclosure, effective treatment of the mononuclear cells with ultraviolet light requires that the collected mononuclear cells be provided in a suspension having a reduced amount of light attenuating material, such as red blood cells. Specifically, the amount of red blood cells in the MNC suspension to be treated affects the amount of UV light that the MNC are exposed to, as the red blood cells in the MNC suspension will block at least a portion the UV light from reaching the targeted MNCs. By way of the present method, the quantity of red blood cells in the suspension is reduced so that a desired amount of UV light will reach the targeted MNC in a more efficient manner. This is preferably achieved by lysing the red blood cells, and removing from the MNC suspension the freed cellular material.

Figure 5:
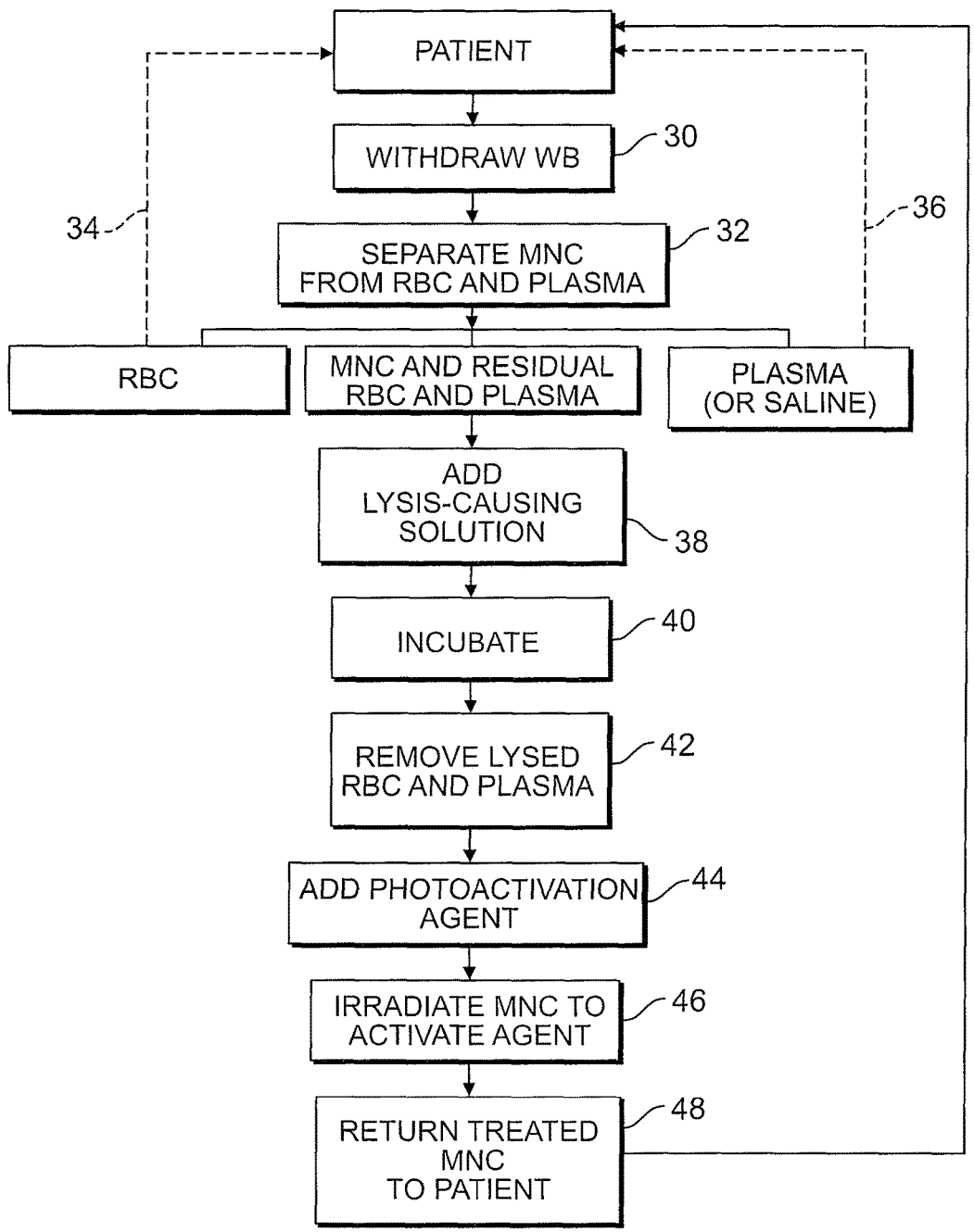
FIG. 5 is a flow chart setting forth the steps of the method of a photopheresis treatment as described herein.

With reference to FIG. 5, a representative method of treating mononuclear cells is seen. A disposable fluid circuit is required that comprises a processing chamber for separating whole blood into one or more components including mononuclear cells, and at least one treatment container adapted to receive mononuclear cells. First, whole blood is withdrawn from a patient (step 30) and introduced into the separation chamber, where the whole blood is subjected to a centrifugal field. The centrifugal field separates the target cell population, i.e., mononuclear cells, from red blood cells, platelets and plasma (step 32). The separated red blood cells and plasma may be returned to the patient (steps 34 and 36), or may be diverted to a container (e.g., container 67) for further processing. However, a residual quantity of red blood cells and plasma typically remains in suspension with the separated mononuclear cells.

The suspension comprising mononuclear cells and residual red blood cells and plasma is then combined with a solution to cause lysis of the red blood cells (step 38). Preferably, ammonium chloride is added to the MNC suspension as an aqueous solution having a concentration of from about 100 mM to 200 mM.

The suspended mononuclear cells with the lysing agent is then incubated to activate the lysing agent and disintegrate or dissolve the red blood cells (step 40). Incubation generally takes from about 3 to 20 minutes, and more typically takes from 10 to 15 minutes. The suspension is then washed with the apheresis device to remove plasma and hemoglobin freed by the lysis of the red blood cells (step 42). Any residual lysing agent is also preferably removed. The washed, lysed suspension is then re-suspended, and combined with an activation agent (step 44), and then exposed to ultraviolet light to obtain a treated cell product (step 46). In one non-limiting example, during treatment, the mononuclear cell product may be exposed to UV bulbs having a wavelength in the UVA range of about 320 nm to 400 nm for a selected period of time, preferably 5 minutes or less, resulting in an average UVA exposure of approximately 0.5-5.0 $J/cm^2$. Alternatively, the red blood cells may be removed from the MNC suspension by using immunogenic cell separation techniques, in which paramagnetic beads coated with antibodies are used to bind the beads to antigens on the surface of the red blood cells, and the suspension is subjected to a magnetic force to separate the red blood cells, or additional density gradient separation (using, e.g., the centrifuge) may be performed.

The treated cell product is then returned to the patient (step 48). Optionally, the treated mononuclear cells may first be returned to separator and concentrated to provide for the concentrated cells to have a smaller total volume as compared to un-concentrated cells. As a result, the smaller volume of concentrated MNCs may be more quickly reinfused to a patient.

Automated control of the MNC collection and the irradiation treatment may be effected by the microprocessor-based controller of the respective separation device 10 and irradiation device 20 with some operator input for each device. Alternatively, operation of both separation device 10 and irradiation device 20 and the process steps carried out by each may be remotely controlled by a separate controller (e.g., a computer) that communicates with both.

As set forth above, the disclosed device includes the aspects set forth below.

In a first aspect, a method of extracorporeal photopheresis of mononuclear cells in a suspension that includes red blood cells is provided that comprises: lysing red blood cells in a suspension; removing from the suspension hemoglobin freed by the lysing of the red blood cells; adding an ultraviolet light activated substance to the suspension; and irradiating the suspension with ultraviolet light.

In a second aspect, the method comprises the addition of a lysing agent to the suspension to effect the lysing.

In a third aspect, the lysing does not substantially adversely affect the viability of the mononuclear cells in the suspension.

In a fourth aspect, the lysing includes addition of ammonium chloride to the suspension.

In a fifth aspect, ammonium chloride is added in an aqueous solution at predetermined concentration.

In a sixth aspect, the predetermined concentration is from about 100 mM to 200 mM.

In a seventh aspect, the suspension includes plasma and the method includes removing plasma from the suspension.

In an eighth aspect, the plasma and hemoglobin are removed substantially simultaneously.

In a ninth aspect, the removing includes washing.

In a tenth aspect, the method further comprises incubating the solution and lysing agent before removing hemoglobin.

In an eleventh aspect, removing hemoglobin is accomplished by centrifuging the solution.

In a twelfth aspect, the suspension is irradiated with ultraviolet light for five minutes or less.

In a thirteenth aspect, the ultraviolet light activated substance comprises psoralen.

In a fourteenth aspect, the ultraviolet light activated substance comprises 8-methoxypsoralen.

In a fifteenth aspect, the suspension is irradiated with UVA ultraviolet light.

In a sixteenth aspect, a method for performing extracorporeal photopheresis of mononuclear cells is provided that comprises: collecting mononuclear cells in a suspension comprising red blood cells and plasma; combining the suspension with a solution to cause lysis of the red blood cells; removing from the suspension plasma and hemoglobin freed by the lysis of the red blood cells; adding an ultraviolet light activated agent to the suspension; and irradiating the suspension with ultraviolet light.

In a seventeenth aspect, removing plasma and hemoglobin freed by the lysis of the red blood cells is accomplished by washing the suspension by centrifugation.

In an eighteenth aspect, the solution for causing lysis of the red blood cells comprises ammonium chloride, and the suspension including the ammonium chloride is incubated.

In a nineteenth aspect, a method of extracorporeal photopheresis of mononuclear cells in a suspension of concentrated mononuclear cells that includes red blood cells and plasma is provided that comprises: removing sufficient red blood cells from the suspension to substantially decrease absorption of ultraviolet light by non-target substances in the suspension; adding an ultraviolet light activated pathogen inactivation substance to the suspension; and, irradiating the suspension with ultraviolet light.

In a twentieth aspect; the red blood cells are removed by either immunomagnetic cell separation or density gradient separation of the suspension.

Thus, systems and methods have been disclosed for preparing a suspension of mononuclear cells such that a prescribed dose of light energy is received and the desired therapeutic effect obtained in a more efficient manner than conventional methods. While the method has been described in the context of the extracorporeal photopheresis of mononuclear cells, it is not limited to the same, as other light dose cell treatment protocols could also utilize this method (i.e., pathogen inactivation).

The invention claimed is:

1. A method for performing extracorporeal photopheresis of mononuclear cells comprising:
   withdrawing whole blood from a human subject;
   introducing said whole blood into a separation chamber of an apheresis device;
   separating mononuclear cells from red blood cells and plasma of said whole blood in said separation chamber;
   collecting a suspension of mononuclear cells, said suspension further comprising at least residual red blood cells and residual plasma;
   withdrawing said red blood cells and plasma that have been separated from said mononuclear cells from said separation chamber;
   combining the collected suspension with a lysing solution;
   incubating the suspension to lyse the residual red blood cells;
   returning said mononuclear cell suspension to said separation chamber of said apheresis device after said withdrawing;
   separating within said apheresis device said mononuclear cells from hemoglobin freed by the lysis of residual red blood cells, residual plasma and any lysing solution in said suspension;
   removing from the suspension residual plasma, hemoglobin freed by the lysis of the red blood cells and any lysing solution by washing the suspension with saline by centrifugation;
   adding an ultraviolet light activated agent to the saline-washed suspension;
   irradiating the saline-washed suspension with ultraviolet light;
   introducing said irradiated suspension into said separation chamber of said apheresis device;
   concentrating the cells so as to have a smaller total volume of said suspension; and
   reinfusing the suspension of concentrated cells having the smaller total volume into the human subject without increasing the total volume with additional plasma.

2. The method of claim 1 wherein the lysing agent does not substantially adversely affect the viability of the mononuclear cells in the suspension.

3. The method of claim 1 wherein the residual plasma and hemoglobin freed by the lysis of the red blood cells are removed substantially simultaneously.

4. The method of claim 1 in which the suspension is irradiated with ultraviolet light for five minutes or less.

5. The method of claim 1 in which the suspension is irradiated with UVA ultraviolet light.

6. The method of claim 1 in which the ultraviolet light activated substance comprises psoralen.

7. The method of claim 6 wherein the ultraviolet light activated substance comprises 8-methoxypsoralen.

8. The method of claim 1 comprising incubating said suspension with said lysing solution for about 3 to 20 minutes.

9. The method of claim 8 comprising incubating said suspension with said lysing solution for 10-15 minutes.

10. The method of claim 1 wherein the lysing solution comprises ammonium chloride.

11. The method of claim 10 wherein the ammonium chloride is added in an aqueous solution at predetermined concentration.

12. The method of claim 11 wherein the predetermined concentration is from about 100 mM to 200 mM.

\* \* \* \* \*